United States Patent [19]

Kobayashi et al.

[11] Patent Number: 5,204,462
[45] Date of Patent: Apr. 20, 1993

[54] 4H-3,1-BENZOXAZIN-4-ONE DERIVATIVE

[75] Inventors: Koji Kobayashi; Koichi Ozawa; Masashi Sasabuchi; Itsuo Uchida, all of Yokohama, Japan

[73] Assignee: Japan Tobacco, Inc., Tokyo, Japan

[21] Appl. No.: 776,372

[22] PCT Filed: Mar. 26, 1991

[86] PCT No.: PCT/JP91/00386
§ 371 Date: Nov. 27, 1991
§ 102(e) Date: Nov. 27, 1991

[87] PCT Pub. No.: WO91/15487
PCT Pub. Date: Oct. 17, 1991

[30] Foreign Application Priority Data

Mar. 30, 1990 [JP] Japan ................... 2-80674

[51] Int. Cl.[5] ............... C07D 265/12; C07D 207/08; C07D 207/46; C07D 5/02
[52] U.S. Cl. .................... 544/92; 548/568; 530/331; 530/332
[58] Field of Search ............ 548/568; 544/92; 530/331, 332

[56] References Cited

U.S. PATENT DOCUMENTS

| | | | |
|---|---|---|---|
| 3,644,350 | 2/1972 | Helsley | 544/92 |
| 4,657,893 | 4/1987 | Krantz | 514/18 |
| 4,745,116 | 5/1988 | Krantz et al. | 544/93 |
| 4,980,287 | 12/1990 | Kokubo et al. | 514/18 |

FOREIGN PATENT DOCUMENTS

| | | |
|---|---|---|
| 60-169469 | 9/1985 | Japan . |
| 62-30770 | 2/1987 | Japan . |
| 979088 | 12/1988 | World Int. Prop. O. . |

OTHER PUBLICATIONS

Teshima et al. (1982) *The Journal of Biological Chemistry*, 257(9):5085–91.

Hedstrom et al. (1984) *Biochemistry*, 23(8):1753–1759.

Spencer et al. (1986) *Biochemical and Biophysical Research Communications*, 140(3):928–33.

*Primary Examiner*—Mukund J. Shah
*Assistant Examiner*—Matthew V. Grumbling
*Attorney, Agent, or Firm*—Birch, Stewart, Kolasch & Birch

[57] ABSTRACT 4H-3,1-benzoxazin-4-one derivatives represented by formula (I) below:

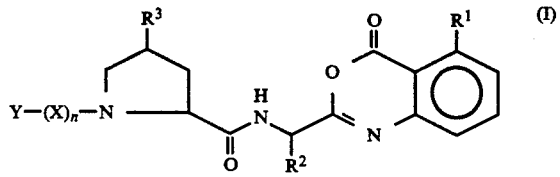

wherein $R^1$ represents a lower alkyl group, $R^2$ represents a lower alkyl group, a lower alkylthioalkyl group, or a lower alkanesulfinylalkyl group, $R^3$ represents a hydrogen atom a hydroxyl group, a lower alkoxy group, or a lower acyloxy group, X represents an amino acid residue selected from the group consisting of alanine, valine, and phenylalanine, n represents an integer of 0, 1, or 2, and Y means a substituent selected from the group consisting of an alkanoyl group having 2 to 6 carbon atoms which may be substituted by a phenyl group, a benzyloxycarbonyl group, a lower alkoxycarbonyl group, a cinnamoyl group, and a methoxysuccinyl group. These derivatives exhibit a strong serine protease inhibiting effect, and are useful as effective components of agents for preventing and curing diseases caused by the excessive effect of serine proteases, e.g., pneumonia, pulmonary emphysema, fibroid lung, bronchitis, arthritis, pancreatitis, nephritis, shock, sepsis, and arteriosclerosis.

2 Claims, No Drawings

4H-3,1-BENZOXAZIN-4-ONE DERIVATIVE

TECHNICAL FIELD

The present invention relates to a novel 4H-3,1-benzoxazin-4-one derivative and, more particularly, to 4H-3,1-benzoxazin-4-one derivatives having a serine protease inhibiting effect.

BACKGROUND ART

Proteases (proteolytic enzymes) present in a living body play a role in the decomposition of extrinsic foreign materials such as bacteria and in removal of decay products of cells. On the other hand, when secretion of proteases, especially serine proteases, is excessively accelerated, degradation and deterioration of tissues are induced in a body. It is, therefore assumed that, in the steady state, proteases maintain a good balance with various intrinsic protease inhibiting substances to maintain homeostasis in a living body. Serine proteases provide a serine residue at their active center for proteolytic activity, and include elastase, chymotrypsin, trypsin, and many other enzymes of individual systems in blood. Particularly, elastase sustains an effect of degrading elastin that exists in and functions to maintain the elasticity of connective tissues such as that of lung, cartilage, tendon, walls of blood vessels, or the skin of higher animals. For example, negative effects have been observed such as pancreatic dysfunction in vivo with pancreatic elastase and other elastases.

Recently, the etiological relation between elastase released from neutrophiles (LE) and the degradation of the extracellular matrix and tissues in inflammatory regions has become clarified. Accordingly, an LE inhibitor is a promising agent for preventing and curing various diseases such as pneumonia, pulmonary emphysema, lung fibrosis, bronchitis, arthritis, pancreatitis, nephritis, shock, sepsis, and arteriosclerosis caused by excessive degradation and deterioration of tissue occurring when LE is excessively produced.

Several compounds have already been reported as serine protease inhibitors such as LE inhibitors. For example, various types of derivatives of a 4H-3,1-benzoxazin-4-one compound are described or disclosed in "Journal of the Biological Chemistry", Vol. 257, pp. 5,085 to 5,091 (1982), "Biochemistry", Vol. 23, pp. 1,753 to 1,759 (1984), "Biochemical and Biophysical Research Communications", Vol. 140, pp. 928 to 933 (1986), Published Unexamined Japanese Patent Application Nos. 60-169469 and 62-30770, and Republication WO 9790/88.

DISCLOSURE OF INVENTION

It is an object of the present invention to provide novel 4H-3,1-benzoxazin-4-one derivatives having a serine protease inhibiting effect and intermediate compounds useful in the manufacture of the same.

The present inventors have conducted extensive studies on various types of derivatives of a 4H-3,1-benzoxazin-4-one compound and found that novel 4H-3,1-benzoxazin-4-one derivatives having a proline residue-containing substituent at its 2-position have an excellent effect in inhibiting serine protease, particularly, elastase, thereby establishing the present invention.

That is, the novel 4H-3,1-benzoxazin-4-one derivatives of the present invention are compounds represented by formula (I) below:

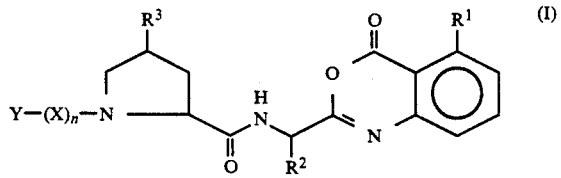

wherein $R^1$ represents a lower alkyl group, $R^2$ represents a lower alkyl group, a lower alkylthioalkyl group, or a lower alkanesulfinylalkyl group, $R^3$ represents a hydrogen atom, a hydroxyl group, a lower alkoxy group, or a lower acyloxy group, X represents an amino acid residue selected from the group consisting of alanine, valine, and phenylalanine, n represents an integer of 0, 1, or 2, and Y represents a substituent selected from the group consisting of an alkanoyl group having 2 to 6 carbon atoms which may be substituted by a phenyl group, a benzyloxycarbonyl group, a lower alkoxycarbonyl group, a cinnamoyl group, and a methoxysuccinyl group.

Intermediate compounds of the present invention are compounds represented by formula (F) below:

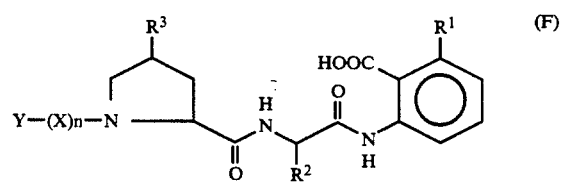

wherein $R^1$ represents a lower alkyl group, $R^2$ represents a lower alkyl group, a lower alkylthioalkyl group, or a lower alkanesulfinylalkyl group, $R^3$ represents a hydrogen atom, a hydroxyl group, a lower alkoxy group, or a lower acyloxy group, X represents an amino acid residue selected from the group consisting of alanine, valine, and phenylalanine, n represents an integer of 0, 1, or 2, and Y represents a substituent selected from the group consisting of an alkanoyl group having 2 to 6 carbon atoms which may be substituted by a phenyl groups a benzyloxycarbonyl group, a lower alkoxycarbonyl group, a cinnamoyl group, and a methoxysuccinyl group.

Note that the definitions and examples of terms describing substituents of the 4H-3,1-benzoxazin-4-one derivatives included in the scope of the present invention, which are referred to in the description of this specification, are as follows.

The "lower alkyl group" in $R^1$ and $R^2$ represents an alkyl group having a straight or branched chain and 1 to 5 carbon atoms. Examples are a methyl group, an ethyl group, a propyl group, an isopropyl group, a butyl group, an isobutyl group, a sec-butyl group, a tert-butyl group, a pentyl group, and an isopentyl group.

Examples of the "lower alkylthioalkyl group" in $R^2$ are a methylthiomethyl group, a methylthioethyl group, an ethylthiomethyl group, an ethylthioethyl group, a 1-(ethylthio)ethyl group, and an isopropylthiomethyl group.

Examples of the "lower alkanesulfinylalkyl group" in $R^2$ are a methanesulfinylmethyl group, a methanesulfinylethyl group, an ethanesulfinylmethyl group, an ethanesulfinylethyl group, a 1-(ethanesulfinyl)ethyl group, and an isopropanesulfinylmethyl group.

The "lower alkoxy group" in $R^3$ can be obtained by etherification of a hydroxyl group. Examples are a methoxy group, an ethoxy group, a propoxy group, an isopropoxy group, a butoxy group, an isobutoxy group, a sec-butoxy group, and a pentyloxy group.

The "lower acyloxy group" in $R^3$ can be obtained by esterification of a hydroxyl group. Examples are an acetoxy group, an ethylcarbonyloxy group, a propylcarbonyloxy group, an isopropylcarbonyloxy group, a butylcarbonyloxy group, an isobutylcarbonyloxy group, a sec-butylcarbonyloxy group, and an isopentylcarbonyloxy group.

Examples of the "alkanoyl group having 2 to 6 carbon atoms which may be substituted by a phenyl group" in Y are a benzylcarbonyl group, a 3-phenylpropionyl group, a 4-phenylbutanoyl group, a 5-phenylpentanoyl group, a 6-phenylhexanoyl group, an acetyl group, a propionyl group, a butanoyl group, a pentanoyl group, and a hexanoyl group. Examples of the "lower alkoxycarbonyl group" in Y are a methoxycarbonyl group, an ethoxycarbonyl group, a propoxycarbonyl group, an isopropoxycarbonyl group, a butoxycarbonyl group, a sec-butoxycarbonyl group, and a tert-butoxycarbonyl group.

Novel 4H-3,1-benzoxazin-4-one derivatives represented by formula (I) according to the present invention can be manufactured in accordance with the following reaction scheme:

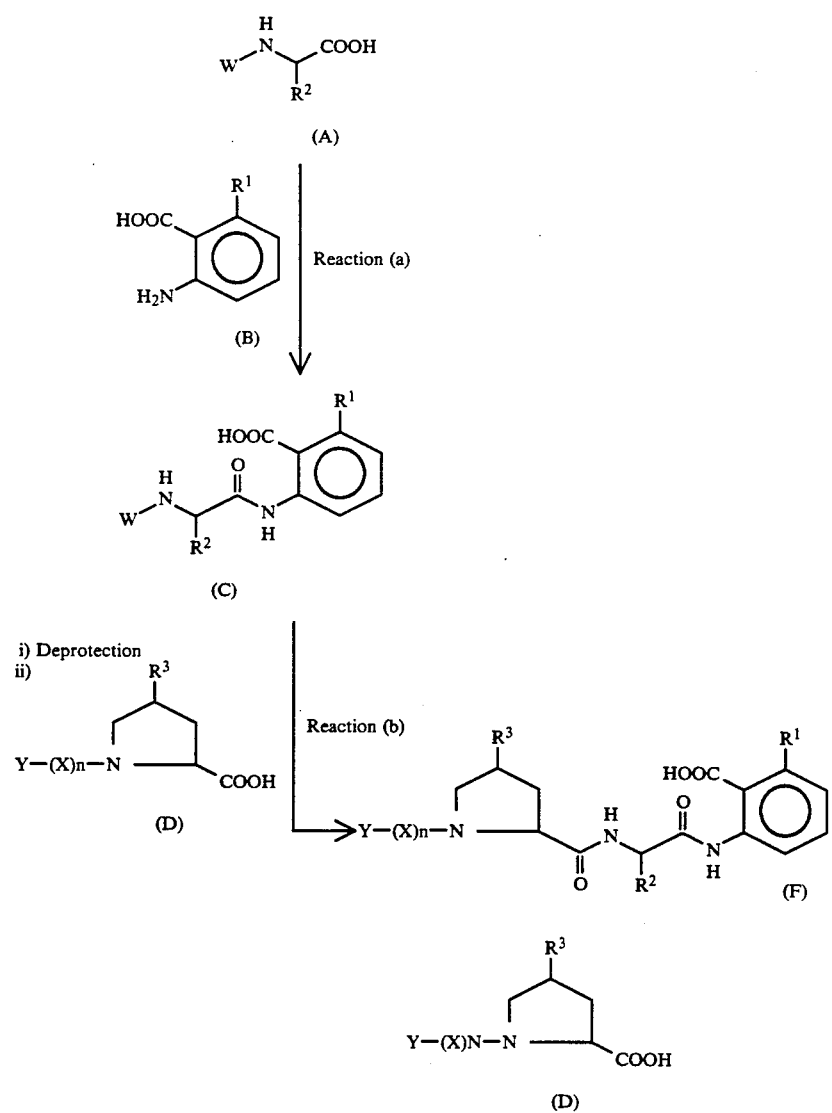

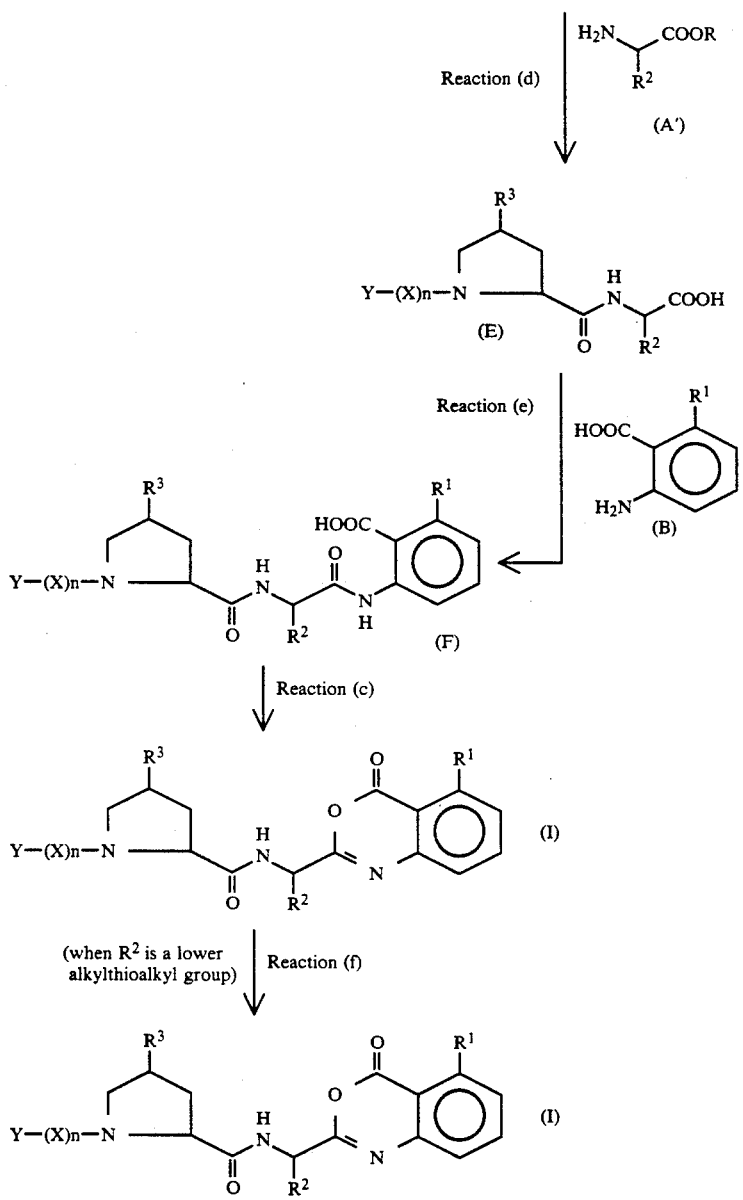

ps (wherein $R^2$ represents a lower alkanesulfinylalkyl group)

In the above reaction scheme, $R^1$, $R^2$, $R^3$ X, Y, and n have the same meanings as described above, W represents an amino protective group normally used in peptide synthesis, e.g., a benzyloxycarbonyl group or a tert-butyloxycarbonyl group, and R represents a hydrogen atom or a carboxyl protective group normally used in peptide synthesis, e.g., an ethyl group or a benzyl group.

Each of steps (a) to (e) illustrated above uses a condensation reaction, and any method known for peptide bond formation in peptide synthesis can be arbitrarily used (e.g., Nobuo Izumiya et al., "Basis and Experiments of Peptide Synthesis", Maruzen K.K.)

The individual steps of the above reaction scheme will be described in detail below in order of the steps.

In the reaction (a), a carboxyl group of an amino acid (A) protected by a suitable protective group (W) is activated by a conventional method and condensed with 6-alkyl-2-aminobenzoic acid (B) to obtain a compound (C). Preferable examples of a condensation method in this reaction are as follows. That is, the amino acid (A) is reacted with a monoalkyl carbonate such as isobutyl chloroformate in the presence of a tertiary amine such as triethylamine or N-methylmorpholine in an inert organic solvent to obtain a mixed acid anhydride. Subsequently, this mixed acid anhydride is condensed with the 6-alkyl-2-aminobenzoic acid (B). Alternatively, the compound (A) is reacted with N-hydroxysuccinimide in the presence of a dehydration condensation agent such as N,N'-dicyclohexylcarbodiimide in an inert organic solvent to obtain an N-hydroxysuccinimide ester. Thereafter, this ester and the 6-alkyl-2-aminobenzoic acid (B) are reacted with each other in the presence of a base such as sodium carbonate in a mixed solvent such as water-acetone, thereby obtaining the compound (C).

In the reaction (b), the amino protective group (W) of the compound (C) is removed by a conventional method to generate a free amino group. A compound having this free amino group and a proline derivative (D) are condensed with each other as in the reaction (a) to obtain a compound (F).

The compound (F) can also be synthesized via the reactions (d) and (e). That is, a carboxyl group of a compound (E) is activated as in the reaction (a) and condensed with the compound (B), thereby obtaining the compound (F). As indicated by the reaction (d), this compound (E) can be synthesized from a compound (A') having a free amino group and the proline derivative (D) by a known peptide bond formation reaction. If R is a hydrogen atom in the compound (A'), the compound (E) can be synthesized by using the method of the reaction (a), i.e., by activating the carboxyl group of the compound (D) and condensing this compound with the compound (A'). If R is a carboxyl protective group, the compound (E) can be synthesized by performing a conventional condensation reaction followed by removal of the protective group In the reaction (c), the compound (F) obtained as described above is cyclized by a dehydration condensation reaction using a condensation agent such as N,N'-dicyclohexylcarbodiimide in an inert organic solvent. As a result, a compound of the present invention represented by formula (I) as a target compound can be obtained.

A compound in which $R^2$ is a lower alkanesulfinylalkyl group in formula (I) can be manufactured from a compound represented by formula (I) in which $R^2$ is a lower alkylthioalkyl group by further performing the reaction (f). In this reaction, for example, a compound represented by formula (I) in which $R^2$ is a lower alkylthioalkyl group is synthesized by the reaction (c) and oxidized at $-20°$ C. to a reflux temperature, and preferably, $0°$ C. to room temperature by using one equivalent of a peracid such as m-chloroperbenzoic acid.

As the inert organic solvent used in each reaction, N,N-dimethylformamide, tetrahydrofuran, dioxane, dimethoxyethane, methylene chloride, and ethyl acetate, for example, can be arbitrarily selected and used.

In order to purify and isolate the target compound from the reaction mixture after the reactions are complete means known in this field of art, e.g., solvent extraction, column chromatography, and recrystallization can be arbitrarily selected and used.

Each of the compounds (A), (A'), and (D) used as the starting material is a known substance or can be synthesized by introducing an amino protective group or a carboxyl protective group to a corresponding known substance and arbitrarily using a known method as the peptide bond formation reaction.

4H-3,1-benzoxazin-4-one derivatives represented by formula (I) of the present invention manufactured by the above method can form pharmacologically acceptable salts. Examples of such salt are acid addition salts with inorganic acids such as hydrochloric acid, sulfuric acid, phosphoric acid, and hydrobromic acid; acid addition salts with organic acids such as tartaric acid, maleic acid, fumaric acid, succinic acid, sulfonic acid; salts of alkali metals such as sodium, potassium, and lithium; and salts of alkali earth metals such as calcium. Any of these compounds are useful as serine protease inhibitors.

In addition, since a 4H-3,1-benzoxazin-4-one derivative represented by formula (I) of the present invention has at least two asymmetric carbon atoms, enantiomer(s) and diastereomers as stereoisomers based on these carbon atoms are present, and cis and trans isomers as geometrical isomers may be present. The scope of the present invention, therefore, includes all of these isomers and their mixtures.

4H-3,1-benzoxazin-4-one derivatives represented by formula (I) of the present invention or their salts can be used as an effective component of a medicinal formulation. Formulations for medicine containing the 4H-3,1-benzoxazin-4-one derivative or its salt are useful as agents for preventing and curing diseases caused by an excessive effect of serine protease, e.g., pneumonia, pulmonary emphysema, lung fibrosis, bronchitis, arthritis, pancreatitis, nephritis, shock, sepsis, and arteriosclerosis.

Formulations for medicine containing a 4H-3,1-benzoxazin-4-one derivative represented by formula (I) of the present invention or its salt as its effective component can be administered by a suitable administration method such as oral administration or parenteral administration. This medicinal formulation can also be administered via the respiratory tract in accordance with the characteristics of a disease with appropriate formulations. Examples of the dosage form for oral administration of this medicinal formulation are a tablet, a capsule, a granule, a powder, and a liquid. Examples of the dosage form for parenteral administration of the formulation are an injection, a suppository, an ointment, and a liquid. In the preparation of these drugs, an excipient, a binder, a disintegrator, and other additives normally used in drugs can be arbitrarily selected and used in accordance with conventional methods. Especially when the medicinal formulation is administered via the respiratory tract, a surfactant and a propellant, for example, can be arbitrarily selected and used to administer the preparation in the form of a meter dose inhalant by propellant means.

More specifically, a tablet having a composition containing a compound of formula (I) of the present invention or its salt as its effective component is manufactured by mixing an excipient such as lactose, starch, or crystalline cellulose, and, if necessary, a binder such as carboxymethylcellulose, methylcellulose, or polyvinylpyrrolidone and/or a disintegrator such as sodium alginate or sodium hydrogencarbonate with effective components, and molding the resultant mixture by a conventional method. In order to manufacture a liquid medicine or a suspension, a glycerol-ester such as tricaprylin or triacetin and an alcohol such as ethanol are mixed with effective components, and a conventional method is applied to the resultant mixture. In order to manufacture a capsule, a granule, powder, or liquid medicine is mixed with a capsule-forming material such as gelatin together with effective components, and a capsule molding method is applied to the resultant mixture.

An injection is manufactured by dissolving effective components in a solvent such as physiological saline, ethanol, or propylene glycol in accordance with whether the injection is an aqueous or nonaqueous solution, and adding an antiseptic agent, a stabilizer, a detergent, and the like if necessary.

As a suppository, a medicinal formulation having a conventional dosage form such as a gelatin soft capsule containing effective components is used.

An ointment, a cream, or the like is formed from effective components and a predetermined carrier in accordance with a conventional method.

A medicinal formulation for aerosol administration can be manufactured by using a pharmaceutically allowable surfactant made from, e.g., an aliphatic acid having 6 to 22 carbon atoms, an aliphatic acid polyvalent alcohol, or a cyclic anhydride thereof, a propellant such as an alkane having 5 carbon atoms or less, or a fluorinated alkane, and effective components.

When a medicinal formulation having a 4H-3,1-benzoxazin-4-one derivative represented by formula (I) or its salt as its effective component is administered to a patient, a dose of 1 to 100 mg/day, as the amount of 4H-3,1-benzoxazin-4-one derivative represented by formula (I), is normally set for an adult. The dose, however, is not limited to this value but is arbitrarily increased or decreased in accordance with the age, the sex, the weight, and the degree of disease of a patient, and the administration method.

BEST MODE FOR CARRYING OUT THE INVENTION

The present invention will be described in more detail below by way of its examples and test examples, but the present invention is not limited to these examples as long as it does not fall outside the scope of the invention.

Example 1

Synthesis of (1'S)-2-[1'-(N-benzyloxycarbonyl-L-prolyl)amino-2-methyl]propyl-5-methyl-4H-3,1-benzoxazin-4-one (a) 2-(N-benzyloxycarbonyl-L-valyl)amino-6-methylbenzoic acid Acetone (18 ml) and N-benzyloxycarbonyl-L-valine N-hydroxysuccinimide ester (8.02 g) were added to an aqueous solution (18 ml) containing 2-amino-6-methylbenzoic acid (3.15 g) and sodium carbonate (2.45 g), and the resultant solution was stirred at room temperature for five hours. The mixture was acidified with 1N hydrochloric acid, and extracted with ethyl acetate. The obtained organic layer was successively washed with 1N hydrochloric acid and brine, dried over sodium sulfate, and concentrated. The residue was purified by silica gel column chromatography to obtain 3.71 g of 2-(N-benzyloxycarbonyl-L-valyl)amino-6-methylbenzoic acid.

(b) 6-methyl-2-(L-valylamino)benzoic acid 2-(N-benzyloxycarbonyl-L-valyl)amino-6methylbenzoic acid (1.21 g) was dissolved in a mixture of methanol (99 ml) and water (1 ml), and 10% Pd-C (200 mg) was added to the solution. The mixture was stirred under a hydrogen atmosphere at room temperature for three hours. After Pd-C was removed by Hyflo-Super-Cel, the filtrate was concentrated to obtain 830 mg of 6-methyl-2-(L-valylamino)benzoic acid.

(c) 2-(N-benzyloxycarbonyl-L-prolyl-L-valyl)amino-6-methylbenzoic acid

Isobutyl chloroformate (0.1 ml) was added dropwise to a tetrahydrofuran solution (2.5 ml) containing N-benzyloxycarbonyl-L-proline (229 mg) and N-methylmorpholine (0.1 ml) at −12° C. to −18° C., and the mixture was stirred at this temperature for nine minutes. An N,N-dimethylformamide solution (1.5 ml) containing 6-methyl-2-(L-valylamino)benzoic acid (142 mg) and N-methylmorpholine (0.075 ml) was added dropwise to the above solution at −15° C., and the resultant solution was stirred at this temperature for 20 minutes and then at room temperature for 45 minutes. Thereafter, 1N hydrochloric acid was added to stop the reaction, and extraction was performed using ethyl acetate. The organic layer was successively washed with 1N hydrochloric acid and brine, dried over sodium sulfate, and concentrated. The residue was purified by flash column chromatography using silica gel to obtain 202 mg of 2-(N-benzyloxycarbonyl-L-prolyl-L-valyl)amino-6-methylbenzoic acid.

(d) (1'S)-2-[1'-(N-benzyloxycarbonyl-L-prolyl)amino-2'-methyl]propyl-5-methyl-4H-3,1-benzoxazin-4-one N,N'-dicyclohexylcarbodiimide (42 mg) was added to an ethyl acetate solution (1 ml) containing 2-(N-benzyloxycarbonyl-L-prolyl-L-valyl)amino-6-methylbenzoic acid (99 mg), and the mixture was stirred at 0° C. for three hours. The precipitated dicyclohexylurea was filtered off, and the filtrate was concentrated. The residue was purified by silica gel column chromatography to obtain (1'S)-2-[1'-(N-benzyloxycarbonyl-L-prolyl)amino-2'-methyl]propyl-5-methyl-4H-3,1-benzoxazin-4-one (89 mg) as a colorless oil.

$^1$HNMR (CDCl$_3$, δ value)
0.81–0.90 (3H, m)
0.97 (3H, d, J=6.8 Hz)
1.85–2.45 (5H, m)
2.74, 2.77 (total 3H, s each)
3.40–3.80 (2H, m)
4.40–4.55 (1H, m)
4.78 (1H, dd, J=5.2 Hz, 8.7 Hz)
5.00–5.30 (2H, m)
6.92 (1H, d, J=8.4 Hz)
7.07 (2H, m)
7.25–7.50 (5H, m)
7.60 (1H, t, J=7.8 Hz) EI-MS (m/z)
463 (M+), 327, 259, 204, 161, 92, 91 (base peak)

EXAMPLE 2

Synthesis of (1'S)-2-[1'-(N-tert-butyloxycarbonyl-L-prolyl)amino-2'--methyl]propyl-5-methyl-4H-3,1-benzoxazin-4-one (a) 2-(N-tert-butyloxycarbonyl-L-prolyl-L-valyl)amino-6-methylbenzoic acid N-tert-butyloxycarbonyl-L-proline N-hydroxysuccinimide ester (258 mg) was added to acetone-water (1 : 1) mixture (8 ml) containing 6-methyl-2-(L-valylamino)benzoic acid (207 mg) and sodium carbonate (90 mg), and the resultant solution was stirred at room temperature for three hours. Water was added to the reaction mixture, and extraction was performed using ethyl acetate. The organic layer was successively washed with a 10% citric acid and brine and concentrated. The residue was purified by silica gel column chromatography to obtain 266 mg of 2-(N-tert-butyloxycarbonyl-L-prolyl-L-valyl)amino-6-methylbenzoic acid.

(b) (1'S)-2-[1'-(N-tert-butyloxycarbonyl-L-prolyl)amino-2'-methyl]propyl-5-methyl-4H-3,1-benzoxazin-4-one N,N'-dicyclohexylcarbodiimide (52 mg) was added to an ethyl acetate solution (1.5 ml) containing 2-(N-tert-butyloxycarbonyl-L-prolyl-L-valyl) amino-6-methylbenzoic acid (121 mg), and the mixture was stirred at 0° C. for two hours. The precipitated dicyclohexylurea was filtered off, and the filtrate was concentrated. The residue was purified by silica gel column chromatography to obtain a white amorphous solid of (1'S)-2-1'-(N-tert-butyloxycarbonyl-L-prolyl)amino-2'-methylpropyl-5-methyl-4H-3,1-benzoxazin-4-one (80 mg).

$^1$HNMR (CDCl$_3$, δ value)
0.97 (3H, d, J=6.3 Hz)

1.01 (3H, d, J=6.8 Hz)
1.39, 1.51 (total 9H, s each)
1.86–2.10 (2H, m)
2.16–2.50 (3H, m)
2.78 (3H, s)
3.65–3.30 (2H, m)
4.34, 4.43 (total 1H, br.s each)
4.79, 4.87 (total 1H, br.s each)
6.92 (0.4H, s)
7.30 (1H, d, J=6.6 Hz)
7.43 (1H, d, J=7.9 Hz)
7.64 (1H, t, J=7.8 Hz)
7.71 (0.6H, d, J=6.9 Hz) EI-MS (m/z)
429 (M+), 373, 356, 328, 259, 217, 202, 189, 170, 160, 114 (base peak)

EXAMPLE 3

Synthesis of
(1'S)-2-[1'-(N-cinnamoyl-L-prolyl)amino-2'-methyl]-propyl-5-methyl-4H-3,1-benzoxazine-4-one (a) N-cinnamoyl-L-proline methyl ester Triethylamine (25.26 ml) and cinnamoyl chloride (16.60 g) were successively added to a methylene chloride solution (300 ml) of L-proline methylester hydrochloride (15.0 g) under ice cooling, and the mixture was stirred under ice cooling for 30 minutes. After stirring at room temperature for 1.5 hours, the mixture was poured into ice water and successively washed with 1N hydrochloric acid, saturated sodium hydrogencarbonate, and saturated salt water, dried over magnesium sulfate, and concentrated. The residue was purified by silica gel column chromatography to obtain 23.09 g of N-cinnamoyl-L-proline methyl ester.

(b) N-cinnamoyl-L-proline 5N sodium hydroxide (18.58 ml) was added dropwise to a methanol solution (100 ml) of N-cinnamoyl-L-proline methyl ester (20.07 g) under ice cooling, and the mixture was stirred at room temperature for three hours. The pH value of the obtained reaction solution was adjusted to 5 with 5N hydrochloric acid, and the resultant solution was poured into 1 l of water. The precipitate was filtered out and dried to obtain 16.84 g of N-cinnamoyl-L-proline.

(c) N-cinnamoyl-L-proline N-hydroxysuccinimide ester

N,N'-dicyclohexylcarbodiimide (2.52 g) was added to an N,N-dimethylformamide solution (25 ml) containing N-cinnamoyl-L-proline (3.00 g) and N-hydroxysuccinimide (1.41 g) under ice cooling, and the mixture was stirred for 20 hours. After the precipitated dicyclohexylurea was filtered off, the filtrate was concentrated. After ethyl acetate was added to the residue and insoluble materials were filtered off, the filtrate was concentrated to obtain 5.11 g of a crude product of N-cinnamoyl-L-proline N-hydroxysuccinimide ester.

(d) 2-(N-cinnamoyl-L-prolyl-L-valyl)amino-6-methylbenzoic acid

An acetone solution (3.9 ml) of N-cinnamoyl-L-proline N-hydroxysuccinimide ester (277 mg) was added dropwise to an aqueous solution (3.9 ml) containing 6-methyl-2-(L-valylamino)benzoic acid (202 mg) and sodium carbonate (86 mg), and the mixture was stirred at room temperature for two hours. The mixture was diluted with water and extracted with ethyl acetate. The organic layer was successively washed with 1N hydrochloric acid, saturated sodium hydrogencarbonate, and brine, dried over sodium sulfate, and concentrated. The residue was purified by silica gel column chromatography to obtain 247 mg of 2-(N-cinnamoyl-L-prolyl-L-valyl)amino-6-methylbenzoic acid.

(e) (1'S)-2-[1'-(N-cinnamoyl-L-prolyl)amino-2'-methyl]propyl-5-methyl-4H-3,1-benzoxazin-4-one N,N'-dicyclohexylcarbodiimide (97 mg) was added to an ethyl acetate solution (2.5 ml) of 2-(N-cinnamoyl-L-prolyl-L-valyl)amino-6-methylbenzoic acid (225 mg) under ice cooling, and the mixture was stirred for two hours. After the precipitated dicyclohexylurea was filtered off, the filtrate was concentrated. The residue was purified by moderate-pressure column chromatography to obtain a white foam of (1'S)-2-[1'-(N-cinnamoyl-L-prolyl)amino-2'-methyl]propyl-5-methyl-4H-3,1-benzoxazine-4-one (121 mg).

$^1$HNMR (CDCl$_3$, δ value).
0.97 (3H, d, J=7.0 Hz)
0.99 (3H, d, J=7.0 Hz)
1.80–2.50 (5H, m)
2.78 (3H, s)
3.64–3.76 (1H, m)
3.76–3.93 (1H, m)
4.77 (1H, dd, J=5.6 Hz, 8.3 Hz)
4.87 (1H, dd, J=1.7 Hz, 8.1 Hz)
6.82 (1H, d, J=15.5 Hz)
7.14 (1H, d, J=7.0 Hz)
7.27 (1H, d, J=7.0 Hz)
7.35–7.61 (6H, m)
7 79 (1H, d, J=15.5 Hz)
7.96 (1H, d, J=8.3 Hz) EI-MS (m/z)
459 (M+), 328, 243, 200, 160, 131 (base peak), 103, 77, 70

EXAMPLE 4

Synthesis of
(1'S)-5-methyl-2-(2'-methyl-1'-[N-(3-phenylpropionyl)-L-prolyl]amino)propyl-4H-3,1-benzoxazin-4-one (a) N-(3-phenylpropionyl)-L-proline benzyl ester N,N'-dicyclohexylcarbodiimide (18.77 g) was added to a methylene chloride solution (250 ml) containing L-proline benzylester hydrochloride (20.00 g), triethylamine (11.53 ml), and 3-phenylpropionic acid (13.67 g), and the mixture was stirred at 0° C. for 20 hours. After the precipitated dicyclohexylurea was filtered off, the filtrate was concentrated. The residue was dissolved in ethyl acetate, and the resultant solution was successively washed with 1N hydrochloric acid, saturated sodium hydrogencarbonate, and brine, dried over magnesium sulfate, and concentrated. The residue was purified by silica gel column chromatography to obtain 26.13 g of N-(3-phenylpropionyl)-L-proline benzyl ester.

(b) N-(3-phenylpropionyl)-L-proline

10% Pd-C (3.00 g) was added to a 1% water-containing methanol solution (200 ml) of N-(3-phenylpropionyl)-L-proline benzyl ester (25.59 g), and the mixture was stirred under a hydrogen atmosphere at room temperature for 2.5 hours. After the catalyst was filtered off, the filtrate was concentrated to obtain 18.93 g of N-(3-phenylpropionyl)-L-proline.

(c) N-(3-phenylpropionyl)-L-proline N-hydroxysuccinimide ester

N,N'-dicyclohexylcarbodiimide (2.75 g) was added to an N,N-dimethylformamide solution (25 ml) containing N-(3-phenylpropionyl)-L-proline (3.00 g) and N- o hydroxysuccinimide (1.40 g), and the mixture was stirred at 0° C. for 20 hours. After the precipitated dicyclohexylurea was filtered off, the filtrate was concentrated to obtain 5.78 g of a crude product of N-(3-phenylpropionyl)-L-proline N-hydroxysuccinimide ester.

(d) 6-methyl-2-{[N-(3-phenylpropionyl)-L-prolyl-L-valyl]amino}benzoic acid

An acetone solution (7.7 ml) of N-(3-phenylpropionyl)-L-proline N-hydroxysuccinimide ester (550 mg) was added dropwise to an aqueous solution (7.7 ml) containing 6-methyl-2-(L-valylamino)benzoic acid (400 mg) and sodium carbonate (169 mg), and the mixture was stirred at room temperature for two hours. The reaction mixture was diluted with water and extracted with ethyl acetate. The organic layer was successively washed with 1N hydrochloric acid, saturated sodium hydrogencarbonate, and brine, dried over magnesium sulfate, and concentrated. The residue was purified by silica gel column chromatography to obtain 456 mg of 6-methyl-2-{[N-(3-phenylpropionyl)-L-prolyl-L-valyl]amino}benzoic acid.

(e) (1'S)-5-methyl-2-{2'-methyl-1'-[N-(3-phenylpropionyl)-L-prolyl]amino}propyl-4H-3,1-benzoxazin-4-one N,N'-dicyclohexylcarbodiimide (171 mg) was added to an ethyl acetate solution (4 ml) of 6-methyl-2-{[N-(3-phenylpropionyl)-L-prolyl-L-valyl]amino}benzoic acid (398 mg), and the mixture was stirred at 0° C. for two hours. After the precipitated dicyclohexylurea was filtered off, the filtrate was concentrated. The residue was purified by silica gel column chromatography to obtain a white foam of (1'S)-5-methyl-2-}2'-methyl-1'-[N-(3-phenylpropionyl)-L-prolyl]amino}propyl-4H-3,1-benzoxazin-4-one (181 mg).

$^1$HNMR (CDCl$_3$, δ value)
0.96 (3H, d, J=7.1 Hz)
1.00 (3H, d, J=7.1 Hz)
1.75-2.45 (5H, m)
2.67 (2H, t, J=7.5 Hz)
2.78 (3H, s)
3.02 (2H, t, J=7.5 Hz)
3.34 (1H, dd, J=9.0 Hz, 16.3 Hz)
3.53 (1H, t, J=9.0 Hz)
4.70-4.80 (2H, m)
7.10-7.30 (6H, m)
7.43 (1H, d, J=8.0 Hz)
7.61 (1H, t, J=8.0 Hz)
7.75 (1H, d, J=7.8 Hz) EI-MS (m/z)
461 (M+), 202, 160, 105, 91 (base peak), 77, 71, 70

EXAMPLE 5

Synthesis of
(1'S)-2-[1'-(N-hexanoyl-L-prolyl)amino-2'-methyl]propyl-5-methyl-4H-3,1-benzoxazin-4-one (a) N-hexanoyl-L-proline benzyl ester Triethylamine (23.1 ml) and hexanoyl chloride (11.4 ml) were added dropwise to a methylene chloride solution (300 ml) of L-proline benzylester hydrochloride (20.00 g) under ice cooling, and the mixture was stirred at room temperature for 1.5 hours. The reaction mixture was successively washed with 1N hydrochloric acid, saturated sodium hydrogencarbonate, and brine, dried over magnesium sulfate, and concentrated to obtain 26.20 g of N-hexanoyl-L-proline benzyl ester.

(b) N-hexanoyl-L-proline

10% Pd-C (3.00 g) was added to a 1% water-containing methanol solution (200 ml) of N-hexanoyl-L-proline benzyl ester (25.61 g), and the mixture was stirred under a hydrogen atmosphere at room temperature for 1.5 hours. After the catalyst was filtered off, the filtrate was concentrated to obtain 17.61 g of N-hexanoyl-L-proline.

(c) N-hexanoyl-L-proline N-hydroxysuccinimide ester

N,N'-dicyclohexylcarbodiimide (3.20 g) was added to an N,N-dimethylformamide solution (25 ml) containing N-hexanoyl-L-proline (3.00 g) and N-hydroxysuccinimide (1.62 g), and the mixture was stirred at 0° C. for 20 hours. After the precipitated dicyclohexylurea was filtered off, the filtrate was concentrated to obtain 6.51 g of a crude product of N-hexanoyl-L-proline N-hydroxysuccinimide ester.

(d) 2-(N-hexanoyl-L-prolyl-L-valyl)amino-6-methylbenzoic acid

An acetone solution (6.8 ml) of N-hexanoyl-L-proline N-hydroxysuccinimide ester (436 mg) was added dropwise to an aqueous solution (6.8 ml) containing 6-methyl-2-(L-valylamino)benzoic acid (352 mg) and sodium carbonate (149 mg), and the mixture was stirred at room temperature for two hours. The reaction mixture was diluted with water and extracted with ethyl acetate. The organic layer was successively washed with 1N hydrochloric acid, saturated sodium hydrogencarbonate, and brine, dried over magnesium sulfate, and concentrated. The residue was purified by silica gel column chromatography to obtain 358 mg of 2-(N-hexanoyl-L-prolyl-L-valyl)amino-6-methylbenzoic acid.

(e) (1'S)-2-[1'-(N-hexanoyl-L-prolyl)amino-2'-methyl]propyl-5-methyl-4H-3,1-benzoxazin-4-one N,N'-dicyclohexylcarbodiimide (112 mg) was added to an ethyl acetate solution (2.5 ml) of 2-(N-hexanoyl-L-prolyl-L-valyl)amino-6-methylbenzoic acid (241 mg), and the mixture was stirred at 0° C. for two hours. After the precipitated dicyclohexylurea was filtered off, the filtrate was concentrated. The residue was purified by silica gel column chromatography to obtain a colorless oil of (1'S)-2-[1'-(N-hexanoyl-L-prolyl)amino-2'-methyl]propyl-5-methyl-4H-3,1-benzoxazin-4-one (164 mg).

$^1$HNMR (CDCl$_3$, δ value)
0.91 (3H, t, J=6.9 Hz)
0.97 (3H, d, J=7.1 Hz)
0.99 (3H, d, J=7.1 Hz)
1.30-1.44 (4H, m)
1.69 (1H, septet, J=7.1 Hz)
1.76-2.08 (2H, m)
2.08-2.25 (2H, m)
2.25-2.50 (4H, m)
2.78 (3H, s)
3.47 (1H, ddd, J=7.1 H, 9.6 Hz, 16.7 Hz)
3.58 (1H, ddd, J=7.1 H, 9.6 Hz, 16.7 Hz)
4.70-4.80 (2H, m)
7.28 (1H, d, J=7.7 Hz)
7.44 (1H, d, J=7.7 Hz)
7.63 (1H, t, J=7.7 Hz)
7.81 (1H, d, J=8.3 Hz) EI-MS (m/z)
427 (M+), 169, 168 (base peak), 160, 113, 71, 70

EXAMPLE 6

Synthesis of
(1'S)-2-[1'-(methoxysuccinyl-L-alanyl-L-alanyl-L-prolyl)amino-2'-methyl]propyl-5-methyl-4H-3,1-benzoxazin-4-one (a) Methoxysuccinyl-L-alanyl-L-alanyl-L-proline N-hydroxysuccinimide ester N,N'-dicyclohexylcarbodiimide (560 mg) was added to an N, N-dimethylformamide solution (10.5 ml) containing methoxysuccinyl-L-alanyl-L-alanyl-L-proline (1.00 g) synthesized by a known method (Castillo et al., "Anal. Biochem.", Vol. 99, pp. 53 to 64, 1979) and N-hydroxysuccinimide (312 mg), and the mixture was stirred at 0° C. to 5° C. for 21 hours. After the precipitated dicyclohexylurea was filtered off, the filtrate was concentrated to obtain 1.28 g of a crude product of methoxysuccinyl-L-alanyl-L-alanyl-L-proline N-hydroxysuccinimide ester.

(b) 2-(methoxysuccinyl-L-alanyl-L-alanyl-L-prolyl-L-valyl)amino-6-methylbenzoic acid An acetone solution (2 ml) of methoxysuccinyl-L-alanyl-L-alanyl-L-proline N-hydroxysuccinimide ester (310 mg) was added to an aqueous solution (2 ml) of 6-methyl-2-(L-valylamino)benzoic acid (165 mg) adjusted to have a pH value of 9.5 by sodium carbonate (70 mg) and 1N hydrochloric acid (0.04 ml), and the mixture was stirred at room temperature for three hours. The reaction mixture was acidified with 1N hydrochloric acid and concentrated. The residue was purified by medium-pressure reverse phase column chromatography using ODS to obtain 181 mg of 2-(methoxysuccinyl-L-alanyl-L-alanyl-L-prolyl-L-valyl)amino-6-methylbenzoic acid.

(c) (1'S)-2-[1'-(methoxysuccinyl-L-alanyl-L-alanyl-L-prolyl)amino-2'-methyl]propyl-5-methyl-4H-3,1-benzoxazin-4-one N,N'-dicyclohexylcarbodiimide (61 mg) was added to an N,N-dimethylformamide solution (1.5 ml) of 2-(methoxysuccinyl-L-alanyl-L-alanyl-L-prolyl-L-valyl)amino-6-methylbenzoic acid (181 mg), and the mixture was stirred at 0° C. for 3.5 hours. The precipitated dicyclohexylurea was filtered off, and the filtrate was concentrated. The residue was successively purified by silica gel column chromatography, preparative thin-layer chromatography, and medium-pressure reverse phase column chromatography to obtain a white solid of (1'S)-2-[1'-(methoxysuccinyl-L-alanyl-L-alanyl-L-prolyl)amino-2'-methyl]propyl-5-methyl-4H-3,1-benzoxazin-4-one (94 mg).

mp 78.5° C. to 80.5° C.

$^1$HNMR (CDCl$_3$, δ value)

0.90 (3H, d, J=6.8 Hz)
0.96 (3H, d, J=6.8 Hz)
1.27 (3H, d, J=6.9 Hz)
1.36 (3H, d, J=6.8 Hz)
1.95–2.38 (5H, m)
2.50–2.63 (2H, m)
2.63–2.74 (2H, m)
2.78 (3H, s)
3.63–3.83 (5H, m)
4.73–4.94 (4H, m)
6.61 (1H, d, J=7.8 Hz)
7.29 (1H, d, J=7.0 Hz)
7.43 (1H, d, J=8.0 Hz)
7.58 (1H, d, J=8.8 Hz)
7.63 (1H, t, J=7.7 Hz)
7.90 (1H, d, J=8.2 Hz) EI-MS (m/z)
585 (M+), 554, 553, 427, 385, 357, 330, 257, 186, 126, 70, 44 (base peak)

EXAMPLE 7

Synthesis of (1'S)-5-methyl-2-{2'-methyl-1'-[N-(5-phenylpentanoyl)-L-prolyl]amino}propyl-4H-3,1-benzoxazin-4-one (a) N-(5-phenylpentanoyl)-L-proline benzyl ester N,N'-dicyclohexylcarbodiimide (12.76 g) was added to a methylene chloride solution (200 ml) containing L-proline benzyl ester hydrochloride (13.58 g), triethylamine (5.69 ml), and 5-phenylvaleric acid (10.01 g) under ice cooling, and the mixture was stirred overnight. The reaction mixture was the treated by the same procedures as in item (a) of Example 4 to obtain N-(5-phenylpentanoyl)-L-proline benzyl ester (15.20 g).

(b) N-(5-phenylpentanoyl)-L-proline

10% Pd-C (1.40 g) was added to a 1% water-containing methanol solution (150 ml) of N-(5-phenylpentanoyl)-L-proline benzyl ester (13.87 g), and the mixture was stirred under a hydrogen atmosphere at room temperature for two hours. After the catalyst was filtered off, the filtrate was concentrated to obtain N-(5-phenylpentanoyl)-L-proline (10.04 g).

(c) N-(5-phenylpentanoyl)-L-proline N-hydroxysuccinimide ester

N,N'-dicyclohexylcarbodiimide (2.25 g) was added to an N,N-dimethylformamide solution (25 ml) containing N-(5-phenylpentanoyl)-L-proline (3.00 g) and N-hydroxysuccinimide (1.25 g) under ice cooling, and the mixture was stirred for 20 hours. After the precipitated dicyclohexylurea was filtered off, the filtrate was concentrated to obtain a crude product (4.80 g) of N-(5-phenylpentanoyl)-L-proline N-hydroxysuccinimide ester.

(d) 6-methyl-2-{[N-(5-phenylpentanoyl)-L-prolyl-L-valyl]amino}benzoic acid

An acetone solution (5 ml) of N-(5-phenylpentanoyl)-L-proline N-hydroxysuccinimide ester (383 mg) was added to an aqueous solution (5 ml) containing 6-methyl-2-(L-valylamino)benzoic acid (257 mg) and sodium carbonate (109 mg), and the mixture was stirred at room temperature for two hours. The reaction mixture was treated by the same procedures as in item (d) of Example 4 to obtain 6-methyl-2-{[N-(5-phenylpentanoyl)-L-prolyl-L-valyl]amino}benzoic acid (351 mg).

(e) (1'S)-5-methyl-2-{2'-methyl-1'-[N-(5-phenylpentanoyl)-L-prolyl]amino}propyl-4H-3,1-benzoxazin-4-one N,N'-dicyclohexylcarbodiimide (129 mg) was added to an ethyl acetate solution (4 ml) of 6-methyl-2-{[N-(5-phenylpentanoyl)-L-prolyl-L-valyl]amino}benzoic acid (318 mg), and the mixture was stirred under ice cooling, for two hours. The reaction mixture was treated by the same procedures as in item (e) of Example 4 to obtain a white foam of (1'S)-5-methyl-2-{2'-methyl-1'-[N-(5-phenylpentanoyl)-L-prolyl]amino}propyl-4H-3,1-benzoxazin-4-one (185 mg).

$^1$HNMR (CDCl$_3$, δ value)

0.93 (3H, d, J=6.8 Hz)
0.96 (3H, d, J=6.8 Hz)
1.7–2.5 (11H, m)
2.65 (2H, t, J=7.3 Hz)
2.78 (3H, s)
3.42 (1H, ddd, J=9.6, 9.6, 7.1 Hz)
3.55 (1H, ddd, J=9.6, 8.6, 2.8 Hz)
4.72 (2H, m)
7.15–7.30 (6H, m)
7.43 (1H, d, J=7.8 Hz)
7.62 (1H, dd, J=7.8, 7.8 Hz)
7.75 (1H, d, J=8.3 Hz) EI-MS (m/z)
489 (M+), 230, 160, 91, 70

EXAMPLE 8

Synthesis of
(1'S)-2-[1'-(N-benzyloxycarbonyl-L-phenylalanyl-L-prolyl)amino-2'-methyl]propyl-5-methyl-4H-3,1-benzoxazin-4-one (a) 2-(N-benzyloxycarbonyl-L-phenylalanyl-L-prolyl-L-valyl)amino-6-methylbenzoic acid Isobutyl chloroformate (0.17 ml) was added to a tetrahydrofuran solution (3.5 ml) containing N-benzyloxycarbonyl-L-phenylalanyl-L-proline (523 mg) and N-methylmorpholine (0.15 ml) at −15° C., and the mixture was stirred for 0.5 hour. An N,N-dimethylformamide solution (5.5 ml) containing 6-methyl-2-(L-valylamino)benzoic acid (220 mg) and N-methylmorpholine (0.12 ml) was added dropwise to the obtained reaction mixture at −15° C., and the mixture was stirred at this temperature for 0.5 hour and then at room temperature for two hours. The reaction mixture was treated by the same procedures as in item (c) of Example 1 to obtain 2-(N-benzyloxycarbonyl-L-phenylalanyl-L-prolyl-L-valyl)amino-6-methylbenzoic acid (317 mg).

(b) (1'S)-2-[1'-(N-benzyloxycarbonyl-L-phenylalanyl-L-prolyl)amino-2'-methyl]propyl-5-methyl-4H-3,1-benzoxazin-4-one N,N'-dicyclohexylcarbodiimide (46 mg) was added to an ethyl acetate solution (3 ml) of 2-(N-benzyloxycarbonyl-L-phenylalanyl-L-prolyl-L-valyl)amino-6-methylbenzoic acid (130 mg), and the mixture was stirred at 0° C. for two hours. The reaction mixture was treated by the same procedures as in item (d) of Example 1 to obtain a white foam of (1'S)-2-[1'-(N-benzyloxycarbonyl-L-phenylalanyl-L-prolyl)amino-2'-methyl]propyl-5-methyl-4H-3,1-benzoxazin-4-one (121 mg).

$^1$HNMR (CDCl$_3$, δ value)
1.00 (3H, d, J=7.0 Hz)
1.03 (3H, d, J=7.0 Hz)
1.7–2.4 (5H, m)
2.79 (3H, s)
2.9–3.1 (2H, m)
3.23 (1H, m)
3.63 (1H, m)
4.64 (1H, m)
4.75 (2H, m)
5.02 (1H, d, J=12.2 Hz)
5.08 (1H, d, J=12.2 Hz)
5.57 (1H, d, J=8.4 Hz)
7.2–7.4 (13H, m)
7.63 (1H, dd, J=7.9, 7.9 Hz) EI-MS (m/z)
610 (M+), 502, 460, 368, 259, 243, 201, 160, 146, 128, 108, 91, 70

EXAMPLE 9

Synthesis of
(1'S)-2-[1'-(N-benzyloxycarbonyl-L-valyl-L-prolyl)amino-2'-methyl]propyl-5-methyl-4H-3,1-benzoxazin-4-one (a) 2-(N-benzyloxycarbonyl-L-valyl-L-prolyl-L-valyl)amino-6-methylbenzoic acid Following the same procedures as in item (a) of Example 8, N-benzyloxycarbonyl-L-valyl-L-proline (459 mg) was condensed with 6-methyl-2-(L-valylamino)benzoic acid (220 mg) to obtain 2-(N-benzyloxycarbonyl-L-valyl-L-prolyl-L-valyl)amino-6-methylbenzoic acid (179 mg).

(b) (1'S)-2-[1'-(N-benzyloxycarbonyl-L-valyl-L-prolyl)amino-2'-methyl]propyl-5-methyl-4H-3,1-benzoxazin-4-one Following the same procedures as in item (b) of Example 8, 2-(N-benzyloxycarbonyl-L-valyl-L-prolyl-L-valyl)amino-6-methylbenzoic acid (169 mg) was subjected to dehydration ring closure using N,N'-dicyclohexylcarbodiimide (55 mg) to obtain a white foam of (1'S)-2-[1'-(N-benzyloxycarbonyl-L-valyl-L-prolyl)amino-2'-methyl]propyl-5-methyl-4H-3,1-benzoxazin-4-one (143 mg).

$^1$HNMR (CDCl$_3$, δ value)
0.96 (3H, d, J=6.7 Hz)
0.99 (3H, d, J=7.1 Hz)
1.01 (3H, d, J=7.1 Hz)
1.03 (3H, d, J=6.7 Hz)
1.9–2.4 (6H, m)
2.78 (3H, s)
3.64 (1H, m)
3.77 (1H, m)
4.37 (1H, dd, J=9.2, 6.3 Hz)
4.67 (1H, dd, J=7.8, 2.7 Hz)
4.75 (1H, dd, J=8.4, 5.5 Hz)
5.08 (1H, d, J=12.2 Hz)
5.03 (1H, d, J=12.2 Hz)
7.25–7.43 (8H, m)
7.63 (1H, dd, J=7.8, 7.8 Hz) EI-MS (m/z)
562 (M+), 454, 412, 357, 259, 223, 195, 160, 108, 91, 79, 70

EXAMPLE 10

Synthesis of
(1'S)-2-[1'-(N-benzyloxycarbonyl-L-prolyl)amino-3'-(methylthio)]propyl-5-methyl-4H-3,1-benzoxazin-4-one (a) 6-methyl-2-[(N-tert-butoxycarbonyl-L-methionyl)amino]benzoic acid After a tetrahydrofuran solution (12.4 ml) of N-tert-butoxycarbonyl-L-methionine (1.24 g) was cooled to −15° C., N-methylmorpholine (0.55 ml) and isobutyl chloroformate (0.60 ml) were added to the solution, and the mixture was stirred for 20 minutes. Subsequently, an N,N-dimethylformamide solution (8.27 ml) containing 2-amino-6-methylbenzoic acid (0.50 g) and N-methylmorpholine (0.44 ml) was added dropwise, and the mixture was stirred at −15° C. for 0.5 hour and then at room temperature overnight. The reaction mixture was treated by the same procedures as in item (c) of Example 1 to obtain 6-methyl-2-[(N-tert-butoxycarbonyl-L-methionyl)amino]benzoic acid (348 mg).

(b) 2-(N-benzyloxycarbonyl-L-prolyl-L-methionyl)amino-6-methylbenzoic acid 6-methyl-2-[(N-tert-butoxycarbonyl-L-methionyl)amino]benzoic acid (346 mg) was dissolved in 4N-hydrochloric acid/dioxane (2.5 ml) stirred at room temperature for two hours. An N,N-dimethylformamide solution (2.5 ml) containing the residue obtained by concentrating and drying the above reaction solution and N-methylmorpholine (0.21 ml) was added to a tetrahydrofuran mixture, and the resultant solution was stirred at −15° C. for 0.5 hour. This tetrahydrofuran mixture was prepared by adding N-methylmorpholine (0.15 ml) and isobutyl chloroformate (0.17 ml) to a tetrahydrofuran solution (3.0 ml) of N-benzyloxycarbonyl-L-proline (328 mg) at −15° C. followed by stirring for 0.5 hour. The resultant reaction mixture was further stirred at room temperature for two hours and treated by the same procedures as in item (c) of Example 1 to obtain 2-(N-benzyloxycarbonyl-L-prolyl-L-methionyl)amino-6-methylbenzoic acid (173 mg).

(c) (1'S)-2-[1'-(N-benzyloxycarbonyl-L-prolyl)amino-3'-(methylthio)]propyl-5-methyl-4H-3,1-benzoxazin-4-one Following the same procedures as in item (d) of Example 1, 2-(N-benzyloxycarbonyl-L-prolyl-L-methionyl)amino-6-methylbenzoic acid (152 mg) was subjected to dehydration using N,N'-dicyclohexylcarbodiimide (61 mg) to obtain a white foam of (1'S)-2-[1'-(N-benzyloxycarbonyl-L-prolyl)amino-3'-(methylthio)]propyl-5-methyl-4H-3,1-benzoxazin-4-one (132 mg).

$^1$HNMR (CDCl$_3$, δ value)
1.9–2.6 (9H, m)
2.06 (3H, s)
2.78 (3H, s)
3.45–3.75 (2H, m)
4.42 (1H, m)
4.85–5.25 (3H, m)
7.1–7.4 (8H, m)
7.62 (1H, dd, J=7.8, 7.8 Hz) EI-MS (m/z)
495 (M+), 421, 286, 189, 160, 81, 70

EXAMPLE 11

Synthesis of (1'R)-2-[1'-(N-benzyloxycarbonyl-L-prolyl)amino-2'-methyl]propyl-5-methyl-4H-3,1-benzoxazin-4-one (a) 2-(N-benzyloxycarbonyl-D-valyl)amino-6-methylbenzoic acid After a tetrahydrofuran solution (40 ml) of N-benzyloxycarbonyl-D-valine (5.08 g) was cooled to −15° C., N-methylmorpholine (2.23 ml) and isobutyl chloroformate (2.61 ml) were added to the solution, and the mixture was stirred for 0.5 hour. An N,N-dimethylformamide solution (25 ml) containing 2-amino-6-methylbenzoic acid (2.04 g) and N-methylmorpholine (1.79 ml) was added dropwise to the above reaction mixture, and the resultant mixture was stirred at −15° C. for 0.5 hour and then at room temperature for two hours. The reaction mixture was treated by the same procedures as in item (c) of Example 1 to obtain 2-(N-benzyloxycarbonyl-D-valyl)amino-6-methylbenzoic acid (1.71 g).

(b) 6-methyl-2-(D-valylamino)benzoic acid

10% Pd-C (70 mg) was added to a 1% water-containing methanol solution (30 ml) of 2-(N-benzyloxycarbonyl-D-valyl)amino-6-methylbenzoic acid (669 mg), and the mixture was stirred under a hydrogen atmosphere at room temperature for two hours. After the catalyst was filtered off, the filtrate was concentrated to obtain 6-methyl-2-(D-valylamino)benzoic acid (347 mg).

(c) 2-(N-benzyloxycarbonyl-L-prolyl-D-valyl)amino-6-methylbenzoic acid 2-(N-benzyloxycarbonyl-L-prolyl-D-valyl)amino-6-methylbenzoic acid (276 mg) was obtained by the same procedures as in item (c) of Example 1 except that 6-methyl-2-(D-valylamino)benzoic acid (346 mg) was used instead of 6-methyl-2-(L-valylamino)benzoic acid.

(d) (1'R)-2-[1'-(N-benzyloxycarbonyl-L-prolyl)amino-2'-methyl]propyl-5-methyl-4H-3,1-benzoxazin-4-one Following the same procedures as in item (d) of Example 1, 2-(N-benzyloxycarbonyl-L-prolyl-D-valyl)amino-6-methylbenzoic acid (241 mg) was subjected to dehydration ring closure using N,N'-dicyclohexylcarbodiimide (103 mg) to obtain a white foam of (1'R)-2-[1'-(N-benzyloxycarbonyl-L-prolyl)amino-2'-methyl]propyl-5-methyl-4H-3,1-benzoxazin-4-one (212 mg).

$^1$HNMR (CDCl$_3$, δ value)
0.75–1.0 (6H, m)
1.85–2.4 (5H, m)
2.78 (3H, s)
3.45–3.8 (2H, m)
4.51 (1H, br.s)
4.82 (1H, dd, J=9.0, 4.9 Hz)
5.15 (1H, d, J=13.2 Hz)
5.23 (1H, d, J=13.2 Hz)
7.25–7.45 (8H, m)
7.61 (1H, br.s) EI-MS (m/z)
463 (M+), 328, 259, 204, 160, 91, 70

EXAMPLE 12

Synthesis of (1'S)-2-[1'-(N-benzyloxycarbonyl-trans-4-hydroxy-L-prolyl)amino-2'-methyl]propyl-5-methyl-4H-3,1-benzoxazin-4-one (a) 2-[(N-benzyloxycarbonyl-trans-4-hydroxy-L-prolyl)-L-valyl]amino-6-methylbenzoic acid Isobutyl chloroformate (0.23 ml) was added to a tetrahydrofuran solution (3.5 ml) containing N-benzyloxycarbonyl-trans-4-hydroxy-L-proline (463 mg) and N-methylmorpholine (0.19 ml) at −15° C., and the mixture was stirred for 0.5 hour. An N,N-dimethylformamide solution (2.5 ml) containing 6-methyl-2-(L-valylamino)benzoic acid (291 mg) and N-methylmorpholine (0.15 ml) was added dropwise to the above mixture at −15° C., and the resultant mixture was stirred at −15° C. for 0.5 hour and then at room temperature for two hours. The reaction mixture was treated by the same procedures as in item (c) of Example 1 to obtain 2-[(N-benzyloxycarbonyl-trans-4-hydroxy-L-prolyl)-L-valyl]amino-6-methylbenzoic acid (570 mg).

(b) (1'S)-2-[1'-(N-benzyloxycarbonyl-trans-4-hydroxy-L-prolyl)amino-2'-methyl]propyl-5-methyl-4H-3,1-benzoxazin-4-one N,N'-dicyclohexylcarbodiimide (201 mg) was added to an ethyl acetate solution (5 ml) of 2-[(N-benzyloxycarbonyl-trans-4-hydroxy-L-prolyl)-L-valyl]amino-6-methylbenzoic acid (485 mg), and the mixture was stirred at 0° C. for two hours. The reaction mixture was treated by the same procedures as in item (d) of Example 1 to obtain a white foam of (1'S)-2-[1'-(N-benzyloxycarbonyl-trans-4-hydroxy-L-prolyl)amino-2'-methyl]propyl-5-methyl-4H-3,1-benzoxazin-4-one (292 mg).

$^1$HNMR (CDCl$_3$, δ value)
0.83 and 0.95 (total 6H, br.s each)
2.05–2.33 (3H, m)
2.49 (1H, br.s)
2.77 (3H, s)
3.55–3.90 (2H, m)
4.58 (2H, m)
4.76 (1H, br.s)
5.17 and 5.54 (total 2H, br.s each)
7.09 (2H, br.s)
7.62 (1H, t, J=7.8 Hz) EI-MS (m/z)
479 (M+), 344, 259, 220, 176, 91

EXAMPLE 13

Synthesis of (1'S)-2-[1'-(N-benzyloxycarbonyl-L-prolyl)amino-3'-(methanesulfinyl)]propyl-5-methyl-4H-3,1-benzoxazin-4-one m-chloroperbenzoic acid (15 mg) was added to a methylene chloride solution (0.5 ml) of (1'S)-2-[1'-(N-benzyloxycarbonyl-L-prolyl)amino-3'-(methylthio)]propyl-5-methyl-4H-3,1-benzoxazine-4-one (41 mg) obtained in Example 10 at 0° C., and the mixture was stirred for 2.5 hours. The reaction mixture was diluted with chloroform and washed with a 10% ice-cooled aqueous sodium sulfite solution and brine, dried over sodium sulfate, and concentrated. The residue was purified by silica gel column chromatography to obtain a white foam of (1'S)-2-[1'-(N-benzyloxycarbonyl-L-prolyl)amino-3'-(methanesulfinyl)]propyl-5-methyl-4H-3,1-benzoxazin-4-one (14 mg).

$^1$HNMR (CDCl$_3$, δ value)
2.0-2.4 (6H, m)
2.54 (3H, s)
2.78 (3H, s)
2.88 (2H, m)
3.45-3.75 (2H, m)
4.3-4.45 (1H, m)
4.8-5.2 (3H, m)
5.70 (1H, br.s)
7.1-7.4 (7H, m)
7.63 (1H, t, J=7.5 Hz) EI-MS (m/z)
511 (M+), 448, 422, 377, 340, 243, 204, 160, 91, 70

Test Example (Inhibitory activity against serine proteases)

In order to investigate the serine protease inhibiting activity of the 4H-3,1-benzoxazin-4-one derivatives according to the present invention, human leukocyte elastase (HLE), bovine α-chymotrypsin (CYT), and human cathepsin G (HCG) were used in accordance with the following methods.

Note that the 4H-3,1-benzoxazin-4-one derivative of the present invention was dissolved in dimethylsulfoxide (DMSO) to adjust to the concentration to 1 mg/ml. This solution was serially diluted with DMSO, and twice the volume of measurement buffer was added to these DMSO solutions to provide the inhibitor solution.

Test 1: Measurement of inhibitory activity against HLE
(Measurement buffer)
0.2M tris-hydrochloride buffer (pH=8.6)
(Enzyme solution)
HLE was purified according to the method described by A. J. Barrett ("Methods in Enzymology", Vol. 80, pp. 581 to 588, 1981) and adjusted to a concentration of 190 nM with measurement buffer. This solution was used as the enzyme solution.
(Substrate solution)
Methoxysuccinyl-L-alanyl-L-alanyl-L-prolyl-L-valyl-paranitroanilide (Funakoshi Co. Ltd., Tokyo, Japan) as enzyme substrate was dissolved and adjusted to a concentration of 5 mM with DMSO. This DMSO solution was diluted with twice the volume of measurement buffer, and then used as the substrate solution.
(Method)
The enzyme solution, the substrate solution, and the inhibitor solution were pre-incubated at 37° C. for 10 minutes. The enzyme solution (140 μl) and the inhibitor solution (30 μl) were mixed in a well of a 96-well microtiter plate (Nunc Co. Ltd., Roskilde, Denmark), and the substrate solutions (30 μl) were added 10 minutes after the mixing, thereby starting the enzyme reaction. Hydrolysis of the substrate was monitored by the measurement of absorbance at 405 nm using a micro plate photometer (Corona Co. Ltd, Tokyo, Japan). The inhibitor concentration at which the activity of HLE was inhibited by 50% (IC$_{50}$) was calculated from the substrate hydrolysis rate in the steady state.

Test 2: Measurement of inhibitory activity against CYT.
(Measurement buffer)
0.2M tris-hydrochloride buffer (pH=8.0)
(Enzyme solution)
CYT (Sigma Co. Ltd., St. Louise, MO) was adjusted to a concentration of 190 nM with the measurement buffer. This solution was used as the enzyme solution.
(Substrate solution)
Methoxysuccinyl-L-alanyl-L-alanyl-L-prolyl-L-phenylalanyl-paranitroanilide (Funakoshi) as the enzyme substrate was dissolved and adjusted to a concentration of 5 mM with DMSO. This DMSO solution was diluted with twice the volume of measurement buffer, and then used as the substrate solution.
(Method)
IC$_{50}$ against CYT was determined in the same procedures detailed in Test 1.

Test 3: Measurement of inhibitory activity against HCG.
(Measurement buffer)
0.2M tris-hydrochloride buffer (pH=7.5)
(Enzyme solution)
HCG (Cosmo Bio Co. Ltd., Tokyo, Japan) was adjusted to a concentration of 190 nM with the measurement buffer. This solution was used as the enzyme solution.
(Substrate solution)
Methoxysuccinyl-L-alanyl-L-alanyl-L-prolyl-L-phenylalanyl-paranitroanilide (Funakoshi) as the enzyme substrate was dissolved and adjusted to a concentration of 5 ml with DMSO. This DMSO solution was diluted with twice the volume of the measurement buffer, and then used as the substrate solution.
(Method)
IC$_{50}$ against HCG was determined in the same procedure detailed in Test 1.

Results:
The results of Tests 1 to 3 are summarized in the following table.

It was confirmed that each compound of the present, invention provide significantly more selective activity in inhibiting certain serine proteases, particularly, human leukocyte elastase, than other serine proteases, e.g., chymotrypsin.

| Example No. | IC$_{50}$ value (μM) | | |
|---|---|---|---|
| | HLE | CYT | HCG |
| 1 | 0.28 | 2.89 | >50 |
| 2 | 2.72 | 18.3 | 26.5 |
| 3 | 1.31 | 15.6 | >200 |
| 4 | 0.52 | 8.69 | >200 |
| 5 | 1.22 | 11.3 | >140 |
| 6 | 2.98 | 22.1 | 15.0 |
| 10 | 0.99 | 4.51 | >50 |
| 12 | 1.15 | 10.7 | >200 |

Taking the above findings together, the novel 4H-3,1-benzoxazin-4-one derivatives described in the present invention provide excellent activity for inhibiting serine proteases, particularly, leukocyte elastase (LE). Accordingly, these compounds are useful as effective protease inhibitors, especially, LE inhibitors for suppressing or curing various inflammatory or deteriorative symptoms such as degradation of tissues and the extracellular matrix caused by the proteolytic effects of protease, particularly, leukocyte elastase, in an animal, especially, a human being.

We claim:

1. 4H-3,1-benzoxazin-4-one derivatives represented by formula (I), below:

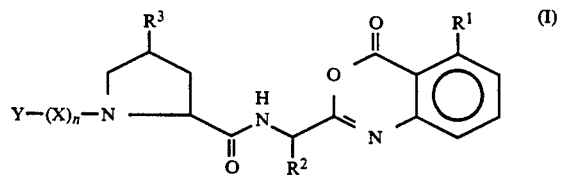

wherein $R^1$ represents a lower alkyl group, $R^2$ represents a lower alkyl group, a lower akylthioalkyl group, or a lower alkanesulfinylalkyl group, $R^3$ represents a hydrogen atom, a hydroxyl group, a lower alkoxy group, or a lower acyloxy group, X represents an amino acid residue selected from the group consisting of alanine, valine, and phenylalanine, n represents an integer of 0, 1, or 2, and Y represents a substituent selected from the group consisting of an alkanoyl group having 2 to 6 carbon atoms which may be substituted by a phenyl group, a benzyloxycarbonyl group, a lower alkoxycarbonyl group, a cinnamoyl group, and a methoxysuccinyl group.

2. Intermediate compounds represented by formula (F) below:

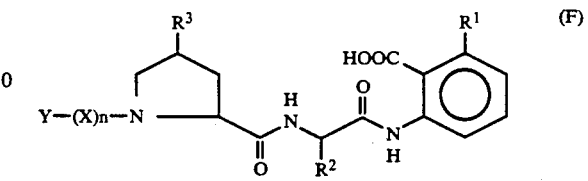

wherein $R^1$ represents a lower alkyl group, $R^2$ represents a lower alkyl group, a lower alkylthioalkyl group, or a lower alkanesulfinylalkyl group, $R^3$ represents a hydrogen atom, a hydroxyl group, a lower alkoxy group, or a lower acyloxy group, X represents an amino acid residue selected from the group consisting of alanine, valine, and phenylalanine, n represents an integer of 0, 1, and 2, and Y represents a substituent selected from the group consisting of an alkanoyl group having 2 to 6 carbon atoms which may be substituted by a phenyl group, a benzyloxycarbonyl group, a lower alkoxycarbonyl group, a cinnamoyl group, and a methoxysuccinyl group.

* * * * *

UNITED STATES PATENT AND TRADEMARK OFFICE
CERTIFICATE OF CORRECTION

PATENT NO. : 5,204,462
DATED : April 20, 1993
INVENTOR(S) : Koji Kobayashi, et al It is certified that error appears in the above-indentified patent and that said Letters Patent is hereby corrected as shown below:

Column 23, line 21, after the formula, change "akylthioalkyl" to --alkylthioalkyl--.

Signed and Sealed this

Tenth Day of May, 1994

BRUCE LEHMAN

Attest:

Attesting Officer

Commissioner of Patents and Trademarks